(12) United States Patent
Katz et al.

(10) Patent No.: US 7,338,470 B2
(45) Date of Patent: Mar. 4, 2008

(54) AIR-BUBBLE-MONITORING MEDICATION ASSEMBLY, MEDICAL SYSTEM AND METHOD

(75) Inventors: Hal H. Katz, West Chester, OH (US); Paul J. Niklewski, Cincinnati, OH (US); Gregory D. Bishop, Hamilton, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 446 days.

(21) Appl. No.: 10/726,845

(22) Filed: Dec. 3, 2003

(65) Prior Publication Data

US 2005/0124929 A1 Jun. 9, 2005

(51) Int. Cl.
*A61M 1/00* (2006.01)
(52) U.S. Cl. ............. 604/122; 604/127; 604/123
(58) Field of Classification Search ............ 604/65, 604/122–124, 127
See application file for complete search history.

(56) References Cited

U.S. PATENT DOCUMENTS

| | | | | |
|---|---|---|---|---|
| 3,935,876 A | * | 2/1976 | Massie et al. | 137/177 |
| 4,565,500 A | | 1/1986 | Jeensalute et al. | |
| 4,756,706 A | * | 7/1988 | Kerns et al. | 604/66 |
| 4,981,467 A | | 1/1991 | Bobo, Jr. et al. | |
| 5,176,631 A | | 1/1993 | Koenig | |
| 5,616,124 A | | 4/1997 | Hague et al. | |
| 6,807,965 B1 | | 10/2004 | Hickle | |

FOREIGN PATENT DOCUMENTS

| | | |
|---|---|---|
| EP | 0 416 911 A2 | 3/1991 |
| GB | 1 392 804 A | 4/1975 |

OTHER PUBLICATIONS

EPO Search Report dated Apr. 13, 2005 for corresponding patent application, European Patent Application No. EP 04 25 7498.

* cited by examiner

*Primary Examiner*—Kevin C. Sirmons
*Assistant Examiner*—Elizabeth MacNeill
(74) *Attorney, Agent, or Firm*—Verne E. Kreger, Jr.

(57) ABSTRACT

An air-bubble-monitoring medication assembly includes a drug infusion subassembly having a tube for administering therein a liquid to a patient, a bubble-size determinator which is positioned to sense an air bubble entrained in the liquid in the tube and which determines the volume of the air bubble, and an analyzer. The analyzer logs the time the detector senses an air bubble and the volume of the air bubble, calculates a running sum of a total air volume of all air bubbles sensed over a time interval, compares the running sum with a preselected limit, and generates an output when the running sum exceeds the preselected limit. The medical system additionally includes a controller assembly which determines a delivery schedule for administering the liquid and which controls the drug infusion subassembly to administer the liquid in accordance with the determined delivery schedule. The method performs the analyzer functions.

14 Claims, 2 Drawing Sheets

AIR-BUBBLE-MONITORING MEDICATION ASSEMBLY, MEDICAL SYSTEM AND METHOD

FIELD OF THE INVENTION

The present invention relates generally to detecting the presence and size of air bubbles entrained in a liquid, and more particularly to a medication assembly, medical system and method involving detecting the presence and size of air bubbles entrained in a liquid being administered to a patient by a drug infusion subassembly.

BACKGROUND OF THE INVENTION

Drug infusion subassemblies are known which have an intravenous tube for administering a liquid, containing a drug, to a patient. Bubble-size determinators are also known which detect the presence of air bubbles above a minimum size entrained in a liquid flowing in an intravenous tube and which determine the volume of the sensed air bubble. Analyzers are known which alarm and/or output a shut-down signal indicating that a drug infusion subassembly is to be shut down if a calculated total bubble size exceeds a predetermined total bubble size over a preselected volume of liquid. The preselected volume of liquid is a preselected number N of liquid volume "windows", wherein an integer is assigned to each of the last N windows corresponding to the total bubble volume of each window, and wherein the integers are summed over the last N windows. If the sum exceeds a fixed amount, an alarm is sent and the drug infusion subassembly is shut down. Data for the previous Nth window is discarded and replaced when data becomes available for the next-to-be-calculated window.

Conscious sedation systems are known which employ a controller for determining (or allow a user, such as a doctor, to determine) a delivery schedule for a conscious sedation drug and for controlling a drug infusion subassembly to intravenously administer the drug depending at least in part on the determined level of sedation of the patient.

What is needed is an improved air-bubble-monitoring medication assembly, and/or an improved medical system, and/or improved method involving monitoring of air bubbles entrained in a liquid being administered by a drug infusion subassembly to a patient. This invention addresses those needs lacking in known air-bubble-monitoring medication assemblies and/or known medical systems, and/or known methods involving monitoring of air bubbles entrained in a liquid being administered by a drug infusion subassembly to a patient.

SUMMARY OF THE INVENTION

A first expression of an embodiment of the invention is for an air-bubble-monitoring medication assembly including a drug infusion subassembly, a bubble-size determinator, and an analyzer. The drug infusion subassembly has a tube for administering therein a liquid to a patient. The bubble-size determinator is positioned to sense an air bubble above a minimum size entrained in the liquid in the tube and determines the volume of the sensed air bubble. The analyzer logs the time the detector senses an air bubble and the volume of the sensed air bubble, calculates a first running sum of a total air volume of all air bubbles sensed over a first time interval, compares the first running sum with a first preselected limit, and generates an output when the first running sum exceeds the first preselected limit.

A second expression of the embodiment of the invention is for a medical system including the air-bubble-monitoring medication assembly as described in the previous paragraph and including a controller assembly which determines a delivery schedule for administering the liquid and which controls the drug infusion subassembly to administer the liquid in accordance with the determined delivery schedule.

A method of the invention is for monitoring air bubbles in a drug infusion subassembly having a tube for administering therein a liquid to a patient. The method includes steps a) through e). Step a) includes disposing a bubble-size determinator to sense the presence of an air bubble above a minimum size entrained in the liquid in the tube, wherein the bubble-size determinator also determines the volume of the sensed air bubble. Step b) includes logging the time the detector senses an air bubble and the volume of the sensed air bubble. Step c) includes calculating a first running sum of a total air volume of all air bubbles sensed over a first time interval. Step d) includes comparing the first running sum with a first preselected limit. Step e) includes generating an output when the first running sum exceeds the first preselected limit.

Several benefits and advantages are obtained from one or more of the expressions of the embodiment and the method of the invention. Using a first running sum of total bubble air volume sensed over a first time interval allows, in one example, the first time interval to be adjusted when the current dose rate changes during a medical procedure as during a medical procedure involving a conscious sedation drug being administered by the drug infusion subassembly. This provides a means to achieve a greater sensitivity of bubble-size monitoring based on the current dose rate. In one implementation, the analyzer also calculates a second running sum of the total bubble air volume sensed over a second time interval, compares the second running sum with a second preselected limit, and generates the output when the second running sum exceeds the second preselected limit. This implementation allows, in one example, having the output be an alarm signal indicating that a total bubble air volume limit has been exceeded and/or a shut-down signal indicating that the drug infusion subassembly is to be shut down when the total volume of air bubbles exceeds 3 volume units in the last 1 time unit or exceeds 4 volume units in the last 2 time units, as can be appreciated by those skilled in the art. This implementation can be extended to include additional running sums, additional preselected limits, and additional time intervals.

The present invention has, without limitation, application in conscious sedation systems used during the performance of medical procedures such as colonoscopies and other endoscopic procedures.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiment of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiment of the present invention for the convenience of the reader and are not for the purpose of limiting the invention.

It is understood that any one or more of the following-described expressions of an embodiment, examples, method, etc. can be combined with any one or more of the other following-described expressions of an embodiment, examples, etc. For example, and without limitation, adjusting of the first time interval based on the current dose rate can be employed in combination with having the output be an alarm signal.

Figure 1:
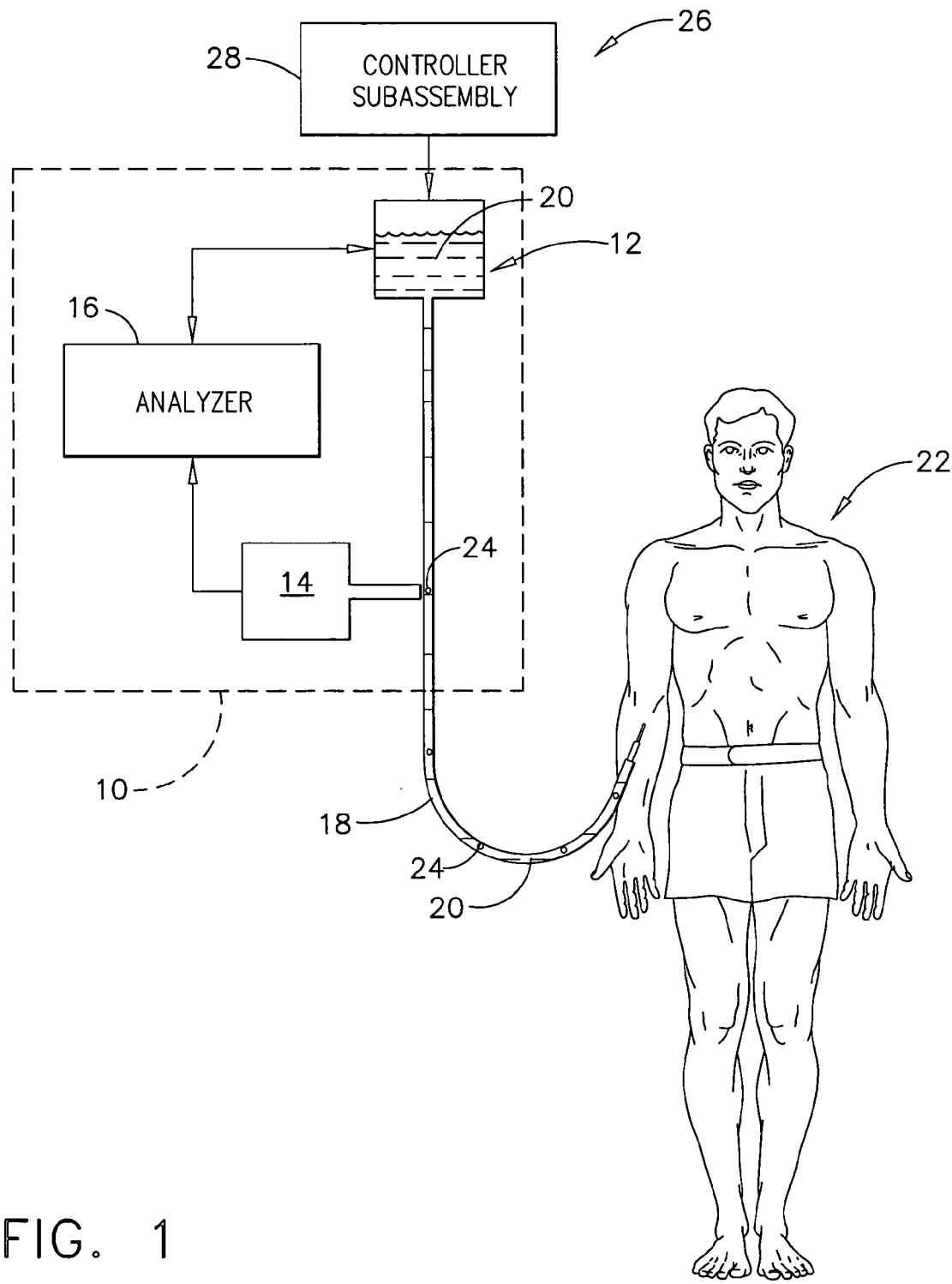
FIG. 1 is a schematic diagram of an embodiment of the present invention showing a medical system, in the form of a conscious sedation system, including a drug infusion subassembly.

Referring now to the drawings, FIG. 1 illustrates an embodiment of the invention. A first expression of the embodiment of FIG. 1 is for an air-bubble-monitoring medication assembly 10 including a drug infusion subassembly 12, a bubble-size determinator 14, and an analyzer 16. The drug infusion subassembly 12 has a tube 18 for administering therein a liquid 20 to a patient 22. The bubble-size determinator 14 is disposed to sense an air bubble 24 above a minimum size entrained in the liquid 20 in the tube 18 and determines the volume (i.e., air volume) of the sensed air bubble 24. The analyzer 16: logs the time the bubble-size determinator 14 senses an air bubble 24 and the volume of the sensed air bubble 24, calculates a first running sum of a total air volume of all air bubbles 24 sensed over a first time interval, compares the first running sum with a first preselected limit, and generates an output when the first running sum exceeds the first preselected limit.

To illustrate the concept of a running sum, assume, as an example, that the first time interval is one minute. Then, the first running sum of the total air volume of all air bubbles 24 sensed over the first time interval is the sum of the total air volume of all air bubbles sensed over the last minute, wherein the first running sum is periodically or continuously updated. In one option the first running sum is updated every ten seconds to reflect the sum of the total air volume of all air bubbles sensed over the previous sixty seconds (i.e., over the last minute). Other updating options are left to the artisan. In one case the minimum size to be exceeded for a sensed air bubble is a non-zero minimum size, and in another case the minimum size to be exceeded for a sensed air bubble is a zero minimum size.

In one known type of bubble-size determinator, the leading and trailing edges of an air bubble are ultrasonically sensed, and the volume of the sensed air bubble is determined from: time clock signals when the leading and trailing edges are sensed, a linear flow rate signal from an intravenous infusion pump type of drug infusion subassembly corresponding to the linear flow rate of the liquid in the tube, and a known model (such as a sphere) of an air bubble. In one variation, the drug infusion subassembly 12, the bubble-size determinator 14 and the analyzer 16 are portions of the same unit. Examples of analyzers 16, include, without limitation, analog and/or digital computers, computer chips, and ASICS (application specific integrated circuits), etc. wherein, without limitation, software, firmware, and/or hardware perform at least logging, calculating, comparing, and output generating functions. In one example, the analyzer 16 logs the times air bubble 24 are sensed and the volumes of the sensed air bubbles 24 in memory locations of a computer memory chip. In one modification, the time an air bubble is sensed for purposes of the analyzer logging that time is the time the bubble-size determinator detects the leading edge or the trailing edge of the bubble (or some average of these two times).

In one implementation of the first expression of the embodiment of FIG. 1, the analyzer 16: calculates a second running sum of a total air volume of all air bubbles 24 sensed over a second time interval; compares the second running sum with a second preselected limit; and generates the output when the second running sum exceeds the second preselected limit, wherein the second time interval is longer than the first time interval, wherein the second preselected limit equals the first preselected limit times a multiplier, and wherein the second time interval does not equal the first time interval times the multiplier. In this implementation, the analyzer 16 generates the output when the total volume of air bubbles exceeds the first preselected limit in the previous first time interval or exceeds the second preselected limit in the previous second time interval. This implementation can, for example, generate an output when the total volume exceeds 3 volume units in the last 1 time unit or exceeds 4 volume units in the last 2 time units, as can be appreciated by those skilled in the art.

In one enablement of the first expression of the embodiment of FIG. 1, the output is a shut-down signal indicating that the drug infusion subassembly 12 is to be shut down and/or an alarm signal indicating a total bubble size limit has been exceeded. In one application, the first time interval is a first predetermined fixed interval. In another application, the drug infusion subassembly 12 administers the liquid 20 at a selectable dose rate, and the first time interval depends on the selected dose rate. In one variation, the analyzer 16 uses a smaller first time interval for a higher selected dose rate and uses a larger first time interval for a lower selected dose rate.

In one illustration of the first expression of the embodiment of FIG. 1, when the drug infusion subassembly 12 has started administering the liquid 20 for a time less then the first time interval, the analyzer 16 calculates an initial sum of a total air volume of all air bubbles 24 sensed up to the first time interval, compares the initial sum with the first preselected limit, and generates the output when the initial sum exceeds the first preselected limit.

In one construction of the first expression of the embodiment of FIG. 1, the tube 18 is an intravenous tube. In one variation, the liquid 20 includes a conscious sedation drug. In one modification, the drug infusion subassembly 12 administers the liquid 20 at a selectable dose rate selected (such as by a user [e.g., a doctor] or a controller assembly) at least in part according to a determined level of sedation of the patient.

A second expression of the embodiment of FIG. 1 is for a medical system 26 including an air-bubble-monitoring medication assembly 10 and a controller assembly 28. The air-bubble-monitoring medication assembly 10 includes a drug infusion subassembly 12, a bubble-size determinator 14, and an analyzer 16. The drug infusion subassembly 12 has a tube 18 for administering therein a liquid 20 to a patient 22. The bubble-size determinator 14 is disposed to sense an air bubble 24 above a minimum size entrained in the liquid 20 in the tube 18 and determines the volume (i.e., air volume) of the sensed air bubble 24. The analyzer 16: logs the time the bubble-size determinator 14 senses an air bubble 24 and the volume of the sensed air bubble 24, calculates a first running sum of a total air volume of all air bubbles 24 sensed over a first time interval, compares the first running sum with a first preselected limit, and generates an output when the first running sum exceeds the first preselected limit. The controller assembly 28 determines a delivery schedule (including any interruption of delivery) including a current dose rate for administering the liquid 20 and controls the drug infusion subassembly 12 to administer the liquid 20 in accordance with the determined delivery schedule. The previously-described implementations, enablements, illustrations, constructions, examples, variations, modifications, etc. of the first expression of the embodiment of FIG. 1 are equally applicable to the second expression.

Figure 2:
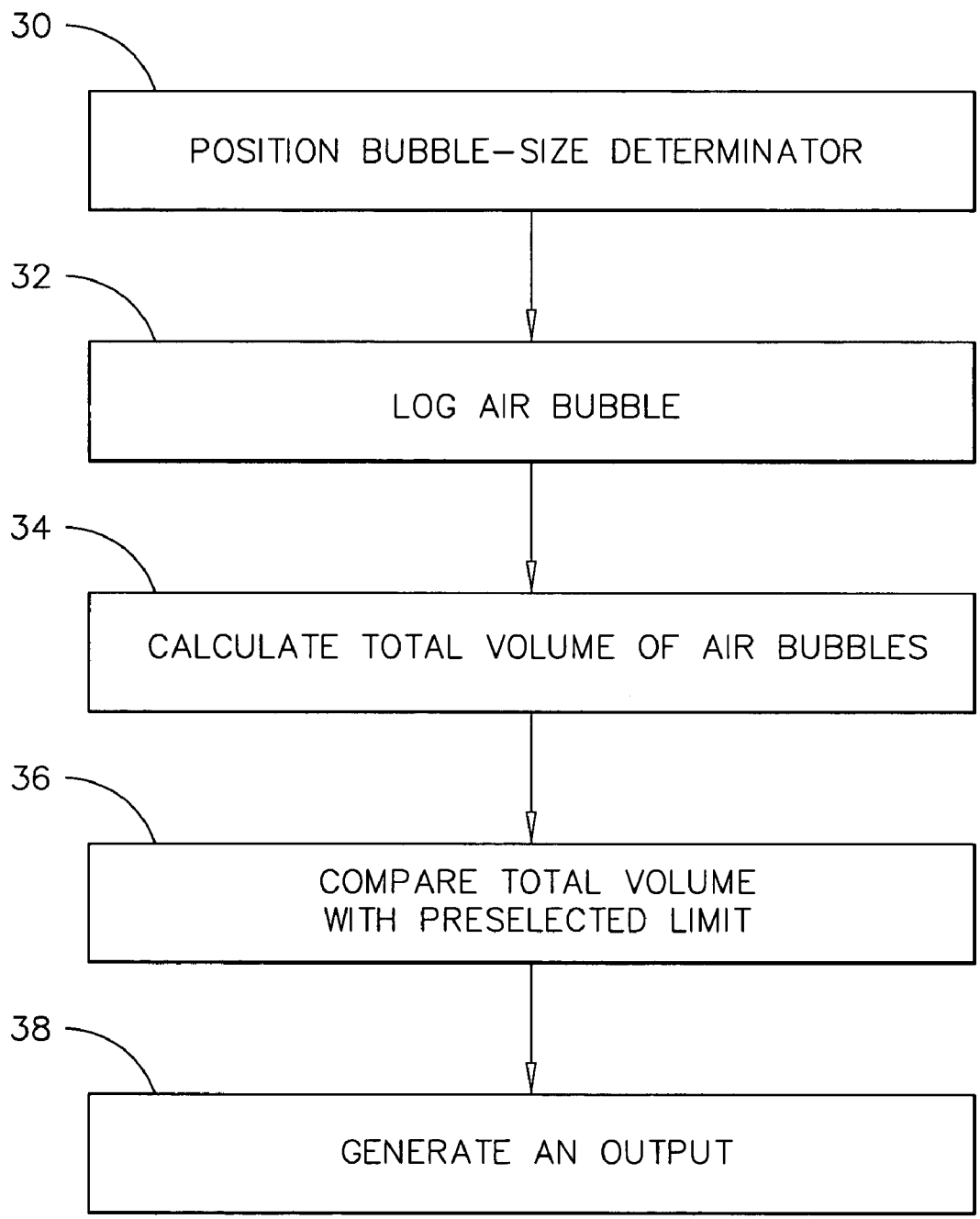
FIG. 2 is a flow chart of a method employing at least some of the components of the embodiment of FIG. 1.

A method of the invention is for monitoring air bubbles 24 in a drug infusion subassembly 12 (such as, but not limited to, the one shown in the embodiment of FIG. 1) having a tube 18 for administering a liquid 20 to a patient 22 and includes steps a) though e). Step a) is labeled as "Position Bubble-Size Determinator" in block 30 of FIG. 2. Step a) includes disposing a bubble-size determinator 14 to sense the presence of an air bubble 24 above a minimum size entrained in the liquid 20 in the tube 18, wherein the bubble-size determinator 14 also determines the volume of the sensed air bubble 24. Step b) is labeled as "Log Air Bubble" in block 32 of FIG. 2. Step b) includes logging the time the bubble-size determinator 14 senses an air bubble 24 and the volume (i.e., air volume) of the sensed air bubble 24 determined by the bubble-size determinator 14. Step c) is labeled as "Calculate Total Volume Of Air Bubbles" in block 34 of FIG. 2. Step c) includes calculating a first running sum of a total air volume of all air bubbles 24 sensed over a first time interval. Step d) is labeled as "Compare Total Volume With Preselected Limit" in block 36 of FIG. 2. Step d) includes comparing the first running sum with a first preselected limit. Step e) is labeled as "Generate An Output" in block 38 of FIG. 2. Step e) includes generating an output when the first running sum exceeds the first preselected limit.

In one implementation of the method, there are included steps f) through h). Step f) includes calculating a second running sum of a total air volume of all air bubbles 24 sensed over a second time interval. Step g) includes comparing the second running sum with a second preselected limit. Step h) includes generating the output when the second running sum exceeds the second preselected limit. The second time interval is longer than the first time interval, the second preselected limit equals the first preselected limit times a multiplier, and the second time interval does not equal the first time interval times the multiplier.

In one operation of the method, the output is a shut-down signal indicating that the drug infusion subassembly is to be shut down and/or an alarm signal indicating a total bubble size limit has been exceeded. In one performance of the method, the drug infusion subassembly 12 administers the liquid 20 at a selectable dose rate, and the first time interval depends on the selected dose rate. The previously-described implementations, enablements, illustrations, constructions, examples, variations, modifications, etc. of the first and/or second expressions of the embodiment of FIG. 1 are equally applicable to the method of the invention.

Several benefits and advantages are obtained from one or more of the expressions of the embodiment and the method of the invention. Using a first running sum of total bubble air volume sensed over a first time interval allows, in one example, the first time interval to be adjusted when the current dose rate changes during a medical procedure as during a medical procedure involving a conscious sedation drug being administered by the drug infusion subassembly. This provides a means to achieve a greater sensitivity of bubble-size monitoring based on the current dose rate. In one implementation, the analyzer also calculates a second running sum of the total bubble air volume sensed over a second time interval, compares the second running sum with a second preselected limit, and generates the output when the second running sum exceeds the second preselected limit. This implementation allows, in one example, having the output be an alarm signal indicating that a total bubble air volume limit has been exceeded and/or a shut-down signal indicating that the drug infusion subassembly is to be shut down when the total volume of air bubbles exceeds 3 volume units in the last 1 time unit or exceeds 4 volume units in the last 2 time units, as can be appreciated by those skilled in the art. This implementation can be extended to include additional running sums, additional preselected limits, and additional time intervals.

The foregoing description of several expressions of an embodiment and a method of the invention has been presented for purposes of illustration. It is not intended to be exhaustive or to limit the invention to the precise forms and procedures disclosed, and obviously many modifications and variations are possible in light of the above teaching. For example, as would be apparent to those skilled in the art, the disclosures herein of the air-bubble-monitoring medication assembly, medical system, components thereof and method therefor have equal application in robotic assisted surgery taking into account the obvious modifications of such systems, components and methods to be compatible with such a robotic system.

What is claimed is:

1. An air-bubble-monitoring medication assembly comprising:
    a) a drug infusion subassembly having a tube for administering therein a liquid to a patient at a dose rate;
    b) a bubble-size determinator which is disposed to sense an air bubble entrained in the liquid in the tube and which determines the volume of the sensed air bubble; and
    c) an analyzer which logs the time the bubble-size determinator senses an air bubble and the volume of the sensed air bubble, which calculates a first running sum of a total air volume of all air bubbles sensed over a first time interval, where the first time interval is dependent upon the dose rate, and the analyzer compares the first running sum with a first preselected limit, and which generates an output when the first running sum exceeds the first preselected limit, and which further calculates a second running sum of a total air volume of all air bubbles sensed over a second time interval; compares the second running sum with a second preselected limit; and generates the output when the second running sum exceeds the second preselected limit, wherein the second time interval is longer than the first time interval, wherein the second preselected limit equals the first preselected limit times a multiplier, and wherein the second time interval does not equal the first time interval times the multiplier.

2. The air-bubble-monitoring medication assembly of claim 1, wherein the output is a shut-down signal indicating that the drug infusion subassembly is to be shut down and/or an alarm signal indicating that a total bubble size limit has been exceeded.

3. The air-bubble-monitoring medication assembly of claim 1, wherein the first time interval is a first predetermined fixed interval.

4. The air-bubble-monitoring medication assembly of claim 1, wherein the analyzer uses a smaller first time interval for a higher selected dose rate and uses a larger first time interval for a lower selected dose rate.

5. The air-bubble-monitoring medication assembly of claim 1, wherein, when the drug infusion subassembly has started administering the liquid for a time less then the first time interval, the analyzer calculates an initial sum of a total air volume of all air bubbles sensed up to the first time interval, compares the initial sum with the first preselected limit, and generates the output when the initial sum exceeds the first preselected limit.

6. The air-bubble-monitoring medication assembly of claim 1, wherein the tube is an intravenous tube.

7. The air-bubble-monitoring medication assembly of claim 1, wherein the liquid includes a conscious sedation drug.

8. The air-bubble-monitoring medication assembly of claim 7, wherein the drug infusion subassembly administers the liquid at a selectable dose rate selected at least in part according to a determined level of sedation of the patient.

9. A medical system comprising:
a) a controller assembly which determines a delivery schedule including a current dose rate for administering the liquid and which controls the drug infusion subassembly to administer the liquid in accordance with the determined delivery schedule;and
b) an air-bubble-monitoring medication assembly including:
1) an intravenous drug infusion subassembly having a tube for administering therein a liquid to a patient;
2) a bubble-size determinator which is disposed to sense an air bubble entrained in the liquid in the tube and which determines the volume of the sensed air bubble; and
3) an analyzer which logs the time the detector senses an air bubble and the volume of the sensed air bubble, which calculates a first running sum of a total air volume of all air bubbles sensed over a first time interval, where the first time interval is dependent upon the dose rate, and the analyzer compares the first running sum with a first preselected limit, and which generates an output when the first running sum exceeds the first preselected limit and which further calculates a second running sum of a total air volume of all air bubbles sensed over a second time interval; compares the second running sum with a second preselected limit; and generates the output when the second running sum exceeds the second preselected limit, wherein the second time interval is longer than the first time interval, wherein the second preselected limit equals the first preselected limit times a multiplier, and wherein the second time interval does not equal the first time interval times the multiplier.

10. The air-bubble-monitoring medication assembly of claim 9, wherein the output is a shut-down signal indicating that the drug infusion subassembly is to be shut down and/or an alarm signal indicating that a total bubble size limit has been exceeded.

11. The air-bubble-monitoring medication assembly of claim 9, wherein, when the drug infusion subassembly has started administering the liquid for a time less then the first time interval, the analyzer calculates an initial sum of a total air volume of all air bubbles sensed up to the first time interval, compares the initial sum with the first preselected limit, and generates the output when the initial sum exceeds the first preselected limit.

12. The air-bubble-monitoring medication assembly of claim 9, wherein the liquid includes a conscious sedation drug, and wherein the drug infusion subassembly administers the liquid at a selectable dose rate selected at least in part according to a determined level of sedation of the patient.

13. A method for monitoring air bubbles in a drug infusion subassembly having a tube for administering therein a liquid to a patient at a dose rate, wherein the method comprises the steps of:
a) disposing a bubble-size determinator to sense the presence of an air bubble entrained in the liquid in the tube, wherein the bubble-size determinator also determines the volume of the sensed air bubble;
b) logging the time the bubble-size determinator senses an air bubble and the volume of the sensed air bubble determined by the bubble-size determinator;
c) calculating a first running sum of a total air volume of all air bubbles sensed over a first time interval where the first time interval is dependent upon the dose rate;
d) comparing the first running sum with a first preselected limit; and
e) generating an output when the first running sum exceeds the first preselected limit;
f) calculating a second running sum of a total air volume of all air bubbles sensed over a second time interval;
g) comparing the second running sum with a second preselected limit; and
h) generating the output when the second running sum exceeds the second preselected limit, wherein the second time interval is longer than the first time interval, wherein the second preselected limit equals the first preselected limit times a multiplier, and wherein the second time interval does not equal the first time interval times the multiplier.

14. The method of claim 13, wherein the output is a shut-down signal indicating that the drug infusion subassembly is to be shut down and/or an alarm signal indicating a total bubble size limit has been exceeded.

* * * * *